US010765131B2

(12) United States Patent
Dierdorp-Andreae et al.

(10) Patent No.: US 10,765,131 B2
(45) Date of Patent: \*Sep. 8, 2020

(54) NISIN PRODUCTION PROCESS

(71) Applicant: Purac Biochem B.V., Gorinchem (NL)

(72) Inventors: Brenda Marja Dierdorp-Andreae, Empel (NL); Jasper Meijer, Breda (NL); Scott Allan McElmury, Bennington, NE (US); Johannes Cornelius Adrianus Blonk, Banglamung (TH); Lansen Court Morehouse, Bennington, NE (US)

(73) Assignee: PURAC BIOCHEM B.V., Gorinchem (NL)

( \* ) Notice: Subject to any disclaimer, the term of this patent is extended or adjusted under 35 U.S.C. 154(b) by 0 days.

This patent is subject to a terminal disclaimer.

(21) Appl. No.: 14/760,990

(22) PCT Filed: Jan. 15, 2014

(86) PCT No.: PCT/NL2014/050014
§ 371 (c)(1),
(2) Date: Jul. 14, 2015

(87) PCT Pub. No.: WO2014/112869
PCT Pub. Date: Jul. 24, 2014

(65) Prior Publication Data
US 2015/0359255 A1 Dec. 17, 2015

Related U.S. Application Data

(60) Provisional application No. 61/752,541, filed on Jan. 15, 2013.

(30) Foreign Application Priority Data

Feb. 26, 2013 (EP) .................................... 13156751

(51) Int. Cl.
| | | |
|---|---|---|
| A23L 3/3463 | (2006.01) | |
| C12P 7/56 | (2006.01) | |
| A23C 9/123 | (2006.01) | |
| C12P 21/02 | (2006.01) | |
| A23L 3/3571 | (2006.01) | |
| A23L 3/3526 | (2006.01) | |
| A23L 3/3535 | (2006.01) | |
| C07K 14/315 | (2006.01) | |

(52) U.S. Cl.
CPC .......... *A23L 3/34635* (2013.01); *A23C 9/123* (2013.01); *A23L 3/3526* (2013.01); *A23L 3/3535* (2013.01); *A23L 3/3571* (2013.01); *C07K 14/315* (2013.01); *C12P 7/56* (2013.01); *C12P 21/02* (2013.01); *A23V 2002/00* (2013.01); *A23Y 2240/41* (2013.01)

(58) Field of Classification Search
CPC .. A23L 3/34635; A23L 3/3526; A23L 3/3571; C12P 21/02

USPC ........................................................... 426/43
See application file for complete search history.

(56) References Cited

U.S. PATENT DOCUMENTS

| | | | |
|---|---|---|---|
| 2,143,361 A | 1/1939 | Morgan et al. | |
| 2,222,520 A | 11/1940 | Sturm | |
| 2,856,326 A | 10/1958 | Shaw | |
| 5,274,152 A | 12/1993 | Carmody | |
| 5,716,811 A * | 2/1998 | Nauth .................. | A23C 9/1236 426/61 |
| 2003/0129715 A1 | 7/2003 | Carlson et al. | |
| 2005/0287272 A1* | 12/2005 | Zheng ................ | A23C 19/0684 426/582 |
| 2007/0020250 A1 | 1/2007 | Tanaka et al. | |
| 2008/0125488 A1 | 5/2008 | Leverve et al. | |
| 2008/0138425 A1 | 6/2008 | Geerse et al. | |
| 2008/0152758 A1* | 6/2008 | Zheng ..................... | A21D 2/24 426/9 |
| 2008/0152764 A1 | 6/2008 | Kremer et al. | |
| 2009/0202448 A1* | 8/2009 | Vorage ..................... | A23L 2/52 424/49 |
| 2010/0062503 A1 | 3/2010 | Visser et al. | |
| 2011/0300220 A1 | 12/2011 | Coszach et al. | |

FOREIGN PATENT DOCUMENTS

| | | |
|---|---|---|
| EP | 1 797 773 A1 | 6/2007 |
| JP | 2502572 B2 | 5/1996 |
| WO | WO-00/28973 A1 | 5/2000 |

(Continued)

OTHER PUBLICATIONS

JP-63-225332—English Abstract—pp. 6-7 (Year: 1988).*
De Vuyst, et al., "Nisin, A lantibiotic produced by *Lactococcus lactis* subsp. *lactis*: properties, biosynthesis, fermentation and applications" In: De Vuyst, L. et al: Bacteriocins of lactic acid bacteria, Chapman Hall (1994) Chapter 5, pp. 151-221.
International Search Report of PCT/NL2014/050014 dated Mar. 21, 2014.
Kalra, et al., "Effect of calcium carbonate on nisin production in a milk culture", Indian Journal of Dairy Science, (1973) vol. 261-15, pp. 146-148.

(Continued)

*Primary Examiner* — Hamid R Badr
(74) *Attorney, Agent, or Firm* — Foley & Lardner LLP

(57) ABSTRACT

The present invention relates to fermentation processes. The objective of the invention was to provide methods for producing nisin containing ferments and formulating such ferments into preservatives. It was in particular an object of the present invention to provide improved processes for producing nisin containing ferments by simple and efficient (batch) culturing and allowing for simple down-stream processing either into a liquid, semi-liquid or a dry powder product, having sufficient nisin content and stability, good handling properties and satisfactory organoleptic properties. Such processes are provided, as well as the products that can be obtained with it and their use as food preservative.

18 Claims, 1 Drawing Sheet

(56) References Cited

FOREIGN PATENT DOCUMENTS

| WO | WO-03/031385 A1 | 4/2003 |
| WO | WO-2010/111680 A2 | 9/2010 |
| WO | WO-2012/030664 A1 | 3/2012 |

OTHER PUBLICATIONS

Perez-Guerra, N. et al., "Production of bacteriocins from *Lactococcuslactis* subsp. *lactis* CECT 539 and pediococcus acidilactici NRRL B-5627 using mussel-processing wastes", Biotechnology and Applied Biochemistry (2002) vol. 36, No. 2, pp. 119-125.

Van'T Hul, et al., "Neutralization/recovery of lactic acid from Lactococcus lactis: effects on biomass, lactic acid, and nisin production", World Journal of Microbiology and Biotechnology (1997) vol. 13, No. 5, pp. 527-532.

"Purasal P HiPure 60 Specification", Internet Citation, Sep. 19, 2002, XP002213995, retrieved from the Internet: URL:http://www.purac.com/products/EN-PHiPure60NPL.PDF.

Lv et al., "Nisin production by *Lactococcus lactis* subsp. *lactis* under nutritional limitation in fed-batch culture", Biotechnology Letters, 2004, vol. 26, pp. 235-238.

\* cited by examiner

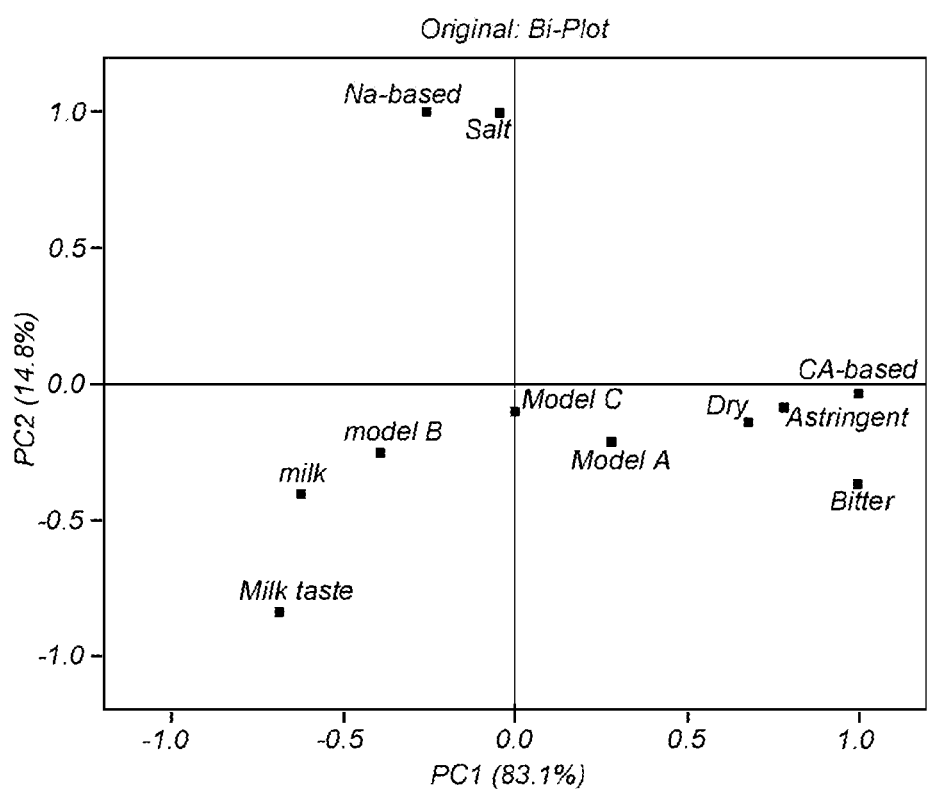

NISIN PRODUCTION PROCESS

CROSS REFERENCE TO RELATED APPLICATIONS

The present application is a National Stage of International Application No. PCT/NL2014/050014 filed on Jan. 15, 2014, which was published on Jul. 24, 2014, as WO 2014/112869 A1, and which claims the benefit of U.S. Application No. 61/752,541 filed Jan. 15, 2013, and which claims the benefit of EP Application No. 13156751.3, filed Feb. 26, 2013, the entire disclosures of which are incorporated herein by reference.

FIELD OF THE INVENTION

The present invention relates to fermentation processes. More in particular, an improved method is provided for the production of lactic acid ferments, which also contain nisin.

BACKGROUND OF THE INVENTION

To prevent decay and quality deterioration of food products, preservatives are commonly added. For decades, chemically synthesized food preservatives have been the primary choice to achieve this goal. More recently, safety issues have been raised with respect to these chemically synthesized food preservatives. Ever since, there has been a growing interest in antimicrobial substances derived from traditional foods.

Lactic acid bacteria are useful microorganisms, which have been traditionally used in the production of various fermented food products. Lactic acid fermentation results in inhibition of the growth of other contaminating bacteria. Due to the pH reduction of the systems with lactic acid produced via lactic acid fermentation, decay and quality deterioration of such food products can be prevented and/or reduced. Additionally, it has been determined that certain additional antimicrobial substances, such as bacteriocins, are produced by some lactic acid bacteria. A known bacteriocin for the control of pathogens in food is nisin. Nisin is produced by *Lactococcus lactis* strains and inhibits a broad range of Gram-positive bacteria. These bacteriocins belong to the lantibiotics group (class I bacteriocins) and have a long history as food preservative.

It is becoming increasingly common to use lactic acid and nisin containing ferments produced by such strains as preservative agents in all kinds of food products.

Conventional bacteriocin fermentation methods are generally inefficient for nisin production on a large (commercial) scale due to limited production rates and unsatisfactory final nisin concentrations. Prolonging the fermentation process also inherently increases the risks of contamination of production batches. More importantly, slow nisin production rates make commercial nisin production costly. Another relevant cost factor is the relatively expensive fermentation medium requirements.

Nisin containing ferments are only exceptionally produced at the same plant where they are also applied to produce the final food products. In most instances nisin containing ferments will be manufactured at one plant to be used, typically some time later, at another plant in the production of the food product. The fermentation products therefore often need to be processed into formulations that can be stored for some time without loss of quality and/or activity, can be transported efficiently and are convenient to handle and to dose in the production of food products. For economic reasons it is often desirable to provide the products in concentrated forms. Such formulations may suitably be liquid, semi-liquid or solid type formulations, each type of formulation having its specific advantages and disadvantages. The most preferred choice will typically vary from one use to another.

The possibilities of producing stable and easy-to-use liquid, semi-liquids and/or solid formulations of nisin containing ferments are to a large extent determined by the thermodynamic behavior of the lactic acid salt(s), constituting the bulk of the ferment. This thermodynamic behavior sets the conditions required for downstream processing into the formulation type of choice, which conditions in turn may have significant impact on the nisin content/activity in the formulation.

Last but not least, organoleptic, dietary and food regulatory requirements additionally put restraints on the fermentation and down-stream processing steps and the types and amounts of the materials to be used therein.

In summary, manufacturers of nisin containing preservative compositions encounter a number of interrelated technological challenges to optimize the process and satisfy the needs and requirements imposed by specific (end-)uses of the product, in particular with regard to production rate and yield, stabilization of the activity, and the processing into stable and easy-to-use formulations. As will be understood, keeping the manufacturing costs at an acceptable level is always a factor in the design of the process.

It is an object of the invention to provide methods for producing nisin containing ferments and formulating such ferments into preservatives. It is in particular an object of the present invention to provide improved processes for producing nisin containing ferments by simple and efficient (batch) culturing and allowing for simple down-stream processing either into a liquid, semi-liquid or a dry powder product, having sufficient nisin content and stability, good handling properties and satisfactory organoleptic properties.

SUMMARY OF THE INVENTION

The present invention provides a process of producing a nisin containing lactate ferment comprising the consecutive steps of:
a) providing a nutrient medium comprising a solution of a fermentable substrate and a nitrogen source in an aqueous medium;
b) inoculating said nutrient medium with nisin producing lactic acid bacteria; and
c) incubating the inoculated nutrient medium nutrient medium under conditions favorable to the growth and/or metabolic activity of said lactic acid bacteria for a period sufficient to produce a fermentation broth containing at least 20 g/l of lactate equivalents and/or at least 1000 IU/ml of nisin equivalent activity, during which period the pH of the fermentation broth is controlled by addition of one or more alkalization agents comprising alkaline sodium and alkaline calcium salts, wherein the Na:Ca (w/w) ratio of the added salts is within the range of ⅙-1/1, preferably within the range of ⅙-½.

In an advantageous embodiment of the invention, the nutrient medium comprises a dairy base, preferably whey.

In an advantageous embodiment of the invention the nutrient medium is inoculated with an inoculation medium comprising activated lactic acid bacteria.

In an advantageous embodiment of the invention the process comprises the additional step d1) of acidification of the fermentation broth by the addition of an acid, preferably lactic acid, in an amount sufficient to reduce the pH of the fermentation broth to below 4.8.

In an advantageous embodiment of the invention, the process comprises the additional step d2) of inactivating the lactic acid bacteria by subjecting the fermentation broth to a temperature of at least 40° C. for a period of at least 10 minutes.

In an advantageous embodiment of the invention the process comprises the additional step e) of concentrating the ferment obtained in step c) or d) to a dry solids content of at least 30 wt. %, preferably within the range of 30-50 wt. %, by evaporation.

In an advantageous embodiment of the invention the process comprises the additional step f) of cooling the concentrate obtained in step e) to a temperature of below 40° C.

In an advantageous embodiment of the invention the process comprises the additional step e') of spray drying the ferment obtained in step c) or d) to produce a free flowing powder.

The present invention also provides the ferments and ferment products obtainable by the above-described method and their various applications as preservatives.

These and other aspects and embodiments of the invention will become apparent to those skilled in the art on the basis of the following detailed description and the experimental work described in the subsequent section.

BRIEF DESCRIPTION OF THE DRAWINGS

FIG. 1 is a Bi-Plot analysis of a taste test of several inventive and comparative examples of products consisting of milk to which nisin and/or lactate ferments have been added with different concentrations of calcium and sodium.

DETAILED DESCRIPTION OF THE INVENTION

As stated herein, the first step a) of the process comprises the preparation of a nutrient medium. In this document, the term "nutrient medium" is used to refer to media in the form originally provided for fermentation. The nutrient medium supplies the substrates and the nutrients the lactic acid bacteria need to grow and to produce the various fermentation products. The nutrient medium typically is an aqueous medium comprising a fermentable substrate, a nitrogen source and micronutrients, wherein the lactic acid bacteria can grow and reproduce. In principle any combination of a carbon source, a nitrogen source and micronutrients may be used as long as it promotes the growth of the lactic acid bacteria.

The term 'fermentation broth' is used herein to refer to the nutrient medium after inoculation with the lactic acid bacteria. Thus, strictly speaking, several types of "fermentation broths" can be distinguished based on the stage to which the fermentation has progressed: (i) nutrient media in the form originally provided including bacteria directly after inoculation; (ii) nutrient media undergoing fermentation wherein some or most of the originally provided nutrients has already been consumed and fermentation products including lactate have been excreted into the media by the bacteria; and, (iii) media that have been removed from the fermentor after part or all of the nutrients have been consumed.

As used herein, the term "fermentable substrate" refers to the carbon source that is converted into another compound by the metabolic action of lactic acid bacteria. As a carbon source, mono-, di-, tri-, oligo and polysaccharides can be used, in particular sugars such as glucose, sucrose, fructose, galactose and lactose and/or starch (hydrolysates). Preferably, in this invention, the substrate is a carbohydrate selected from the group consisting of lactose, sucrose and glucose, most preferably lactose.

These carbohydrates can be derived from a variety of sources, such as dairy products and plant, fruit or vegetable derived products, e.g. molasses, fruit or vegetable juices, fruit or vegetable pulp, etc. The invention can be practiced using one or more carbohydrates in partly or substantially purified form. Alternatively, the invention can practiced using a raw material containing one or more carbohydrates.

The nutrient medium typically contains at least 1 g/l, more preferably 5-300 g/l, most preferably 10-80 g/l, of the carbohydrate.

Suitable examples of nitrogen sources include plant derived protein, such as soy protein and pea protein, dairy protein, yeast or yeast extract, meat extract, various kinds of fermentation fungi, as well as hydrolysates of any of the afore mentioned proteins. It is preferred that the nitrogen source comprises free amino acids and/or short peptides. Suitable nitrogen sources may be prepared by hydrolysing a protein source. In one embodiment of the invention the nitrogen source is selected from the group consisting of pea protein, yeast extracts and dairy protein hydrolysates, more preferably yeast extracts and dairy protein hydrolysates, especially casein hydrolysate.

The nutrient medium typically contains at least 0.1 g/l, more preferably 0.2-50 g/l, most preferably 0.5-20 g/l of the nitrogen source. These amounts refer to the total dry solids weight of the material added as the nitrogen source per liter of nutrient medium, as will be understood by those skilled in the art. Hence, the nutrient medium typically contains at least 0.1 g/l, more preferably 0.2-50 g/l, most preferably 0.5-20 g/l of proteins, peptides and/or free amino acids.

In some embodiment of the invention, the nutrient medium further comprises micronutrients that support the growth metabolic action of the lactic acid bacteria, such as vitamins, minerals, co-factors and/or other trace-elements. The micronutrients are generally used at a rate of at least 0.01% (w/v), preferably at a rate of between 0.1 and 2% (w/v) in the nutrient medium. Typically, the carbohydrate sources and/or nitrogen sources that may be used in accordance with the invention inherently contain micronutrients.

A particularly preferred embodiment of the invention concerns the fermentation of a dairy product. As used herein, the term "dairy product" refers to whole (animal) milk, components of the milk as well as products derived from milk, such as whey, whey permeate, milk permeate, yoghurt and quark and by-products from the preparation of yoghurt and quark. In some preferred embodiments, by volume, the major component of the nutrient medium is the dairy product. In some embodiments, the nutrient medium comprises at least 80%, at least 90%, at least 95%, at least 99%, or at least 99.9% of the volume of milk, e.g. a product selected from whole milk, raw milk, skim milk, reconstituted milk, condensed milk, re-hydrated milk and the like. In some embodiment, the nutrient medium comprises at least 80%, at least 90%, at least 95%, at least 99%, or at least 99.9% of the dry solids weight of milk solids, e.g. whole milk solids, raw milk solids, skim milk solids, whey and the like. In a particularly preferred embodiment said milk solid is whey.

Another preferred embodiment of the invention concerns the fermentation of a fruit or vegetable derived product, such as fruit or vegetable derived juices, pastes or pulp. In some preferred embodiments, by volume, the major component of the nutrient medium is the fruit or vegetable derived product.

Suitable examples include tomato, carrot, spinach, molasses, etc. In a particularly preferred embodiment of the invention the fruit or vegetable derived product is a juice obtained by mechanically squeezing or macerating the raw fruit or vegetable. In some embodiments, the fruit or vegetable derived product comprises at least 80%, at least 90%, at least 95%, at least 99%, or at least 99.9% of the volume of the nutrient medium. In some embodiments, the nutrient medium comprises at least 80%, at least 90%, at least 95%, at least 99% of the dry solids weight of fruit or vegetable solids.

As stated herein, the subsequent step b) comprises inoculating the nutrient medium with nisin producing lactic acid bacteria.

In accordance with this invention, the "lactic acid bacteria" are capable of producing nisin. In some preferred embodiments, the lactic acid bacteria belong to the order *Lactobacillales*, preferably to the *Lactococcus* genus. The lactic acid bacteria producing nisin most preferably belong to *Lactococcus lactis* ssp. *lactis*, and examples thereof include JCM 7638, ATCC 11454, NCDO 497 and IFO 12007. In preferred embodiments, the lactic acid bacteria are lactic acid bacteria that have GRAS status.

In some embodiments, the fermentation broth comprises a single species of nisin producing lactic acid bacteria, while in other embodiments, the fermentation broth comprises a mixture of lactic acid bacteria strains, at least one of which is capable of producing nisin. In one embodiment mixtures of nisin producing lactic acid bacteria strains are used.

In one embodiment the nutrient medium is inoculated with a fermentation broth comprising activated lactic acid bacteria. The term 'activated' is used herein to indicate that the composition used to inoculate the nutrient medium comprises lactic acid bacteria in a metabolically active state. When the bacteria are introduced into the nutrient medium during direct seeding i.e. in the form of a dry, liquid or frozen concentrate, the bacteria do not take effect straight away and require time to become active. This 'time lag', also referred to as 'lag phase', may involve re-establishment of the stored bacteria into the natural form (rehydration phase of the bacteria), restoration of the metabolic activity and/or adaptation to the new environment. In accordance with a preferred embodiment of this invention, the inoculation of the (production) nutrient medium is done with a fermentation broth comprising activated lactic acid bacteria, which typically shortens the lag phase, which can significantly decrease the overall fermentation time. The use of activated lactic acid bacteria may also increase the rate of reproduction during the exponential phase and/or the rate of lactic acid and/or nisin production during the exponential and/or stationary phases of the fermentation process.

In one embodiment of the invention, a fermentation broth comprising activated lactic acid bacteria is used for inoculating the nutrient medium, wherein the broth comprises more than 12 g/l of lactate equivalents, more preferably more than 14 g/l, most preferably more than 16 g/l. As used herein, the term "lactate equivalent" refers to the total of the free lactic acid and the conjugated base (dissociated acid), as will be understood by those of ordinary skill. The terms "lactic acid" and "free lactic acid" are employed interchangeably herein to refer to the acid form. The term lactate refers to the dissociated form of lactic acid. The (dissolved) salt of lactate is also specifically referred to herein as "lactate salt".

In one embodiment of the invention, the fermentation broth comprising activated lactic acid bacteria used for inoculating the nutrient medium is prepared by incubating the lactic acid bacteria in an activation medium, which is similar in composition to the production nutrient medium. In one embodiment of the invention, the activation medium has the same composition as the production nutrient medium. In one particularly preferred embodiment of the invention, the activation medium is enriched as compared to the production nutrient medium, preferably one or more nutrients applied in the production nutrient medium are used in excess amounts in the activation medium, typically meaning that the concentration is at least 120% of the concentration employed in the nutrient medium. More preferably the activation medium comprises one or more of said nutrients in concentrations of at least 130% of the concentrations employed in the production nutrient medium, even more preferably at least 140%. In a particularly preferred embodiment of the invention the nitrogen source is used in excess amounts in the activation medium.

As will be understood by those skilled in the art the fermentation broth comprising activated lactic acid bacteria can be prepared using standard equipment and methodology.

As stated herein, the process comprises a step c), wherein the inoculated nutrient medium is incubated to produce a fermentation broth comprising lactate and nisin. Production-scale lactic acid fermentation requires strict control of fermentation conditions, in particular of the pH. Without control of the pH, the formation of lactic acid as a product of the metabolic action of the lactic acid producing bacteria, the pH will decrease as the fermentation proceeds. A drop in pH below a critical value, depending on the microorganism used in the process, could negatively affect the microorganism's metabolic process and eventually bring the fermentation process to a stop. The exact critical value will depend on the specific set of incubation conditions. In general, it is preferred that, during the incubation step, the pH of the fermentation broth is maintained within the range of 4.5 to 8.0, preferably within the range of 4.8 to 6.5, more preferably within the range of 5.0-6, e.g. 5.5, in order to prevent Inhibition of lactate production. Inhibition of lactate production is considered to have occurred when the amount of lactate produced in (batch) fermentation does not increase by more than about 3% upon further incubation for a period of up to about twelve hours under the same conditions. This definition presumes that sufficient nutrients for lactate production are still available in the fermentation broth and applies to both batch and continuous operations.

As mentioned before, prevention of the pH drop to below the critical value is accomplished by adding one or more alkalization agents comprising alkaline sodium and calcium salts. Alkalization, as used herein, refers to the effect of lowering the amount of acid in a solution to any extent and, hence, increasing the pH value. It does not imply an increase of the pH to above neutral. As such the term 'alkalization' is deemed to be synonymous to and interchangeable with 'neutralization'. The term "alkaline salt" means an organic or inorganic salt of the respective alkaline metal or alkaline earth metal, which reacts with an acid to accept hydrogen atoms and/or donate a pair of valence electrons, and, as such, can be added to the fermentation broth to increase the pH to the desired value. Examples of the alkaline salts in accordance with the invention include the hydroxides of sodium and calcium, carbonates of sodium and calcium. In a preferred embodiment of the invention the one or more alkalization agents comprise sodium hydroxide and calcium hydroxide.

The invention in part resides in the finding that it is advantageous to use both sodium and calcium salts as alkalization agent and especially to combine sodium and calcium salts in amounts resulting in a Na:Ca ratio (w/w) within the range of 1/6-1/1. In a more preferred embodiment of the invention, the Na:Ca (w/w) ratio is within the range of 1/6-1/2, more preferably within the range of 1/5.5-1/2.5, most preferably the Na:Ca (w/w) ratio is within the range of 1/5-1/3, e.g. 1/4.

As will be understood by those skilled in the art, in the context of this invention it is not critical whether or not the sodium and calcium salts are mixed before addition to the ferment. It is envisaged that the sodium and calcium salts are added separately to the ferment, which can be done simultaneously or subsequently. For practical reasons it is however preferred to pre-mix the sodium and calcium salts, as will be understood by those skilled in the art. Hence, the present process typically comprises the addition of an alkalization comprising a mixture of alkaline sodium and calcium salts in relative amounts yielding the above recited ratios of sodium and calcium ions. In an even more preferred embodiment of the invention, an alkalization agent is added in the form of an aqueous solution of the alkaline sodium and calcium salts in relative amounts yielding the above recited ratios of sodium and calcium ions, e.g. an aqueous solution of 2.5-20% (w/v) sodium hydroxide, preferably 3-10% (w/v), e.g. about 5% w/v, and 5-40% (w/v) calcium hydroxide, preferably 10-30% (w/v), e.g. about 20% (w/v).

It is also envisaged that other alkalizing agents may be used in conjunction with the alkaline sodium and calcium salts. For example, other alkali or earth alkali metal hydroxides, such as potassium hydroxide, may be added in addition. Typically such other alkalizing agents are used only in minor amounts. It is preferred that the alkaline sodium and calcium salts are used in such amounts that at least 75% of the total mol amount of alkali and earth alkali metal ions added is calcium and sodium, more preferably at least 80%, at least 85%, at least 90%, at least 95%, or at least 97%.

As will be understood by those of ordinary skill in the art, pH control will typically involve continuous or repeated administration of alkalizing agent. The process is preferably automated for precise control of the pH at a predetermined value.

Fermentation generally will be conducted at temperatures conventionally employed in lactic acid fermentation processes. Temperatures in the range of 20° C. to 40° C. typically will be employed, with temperatures in the range of 20° C. to 35° C., such as about 30° C., being preferred.

Under the conditions described herein, production-scale fermentations can be performed with a duration typically varying between 10-24 hours, although the invention is not particularly limited in this respect. Shorter fermentation times are generally preferred as it inherently reduces the risks of the fermentation broth becoming contaminated with other microbiological species.

The incubation can be performed using standard equipment for batch and/or continuous processing. Typically the process is performed in a (standard) production fermentor comprising a vessel having a volume of at least 250 L, at least 500 L or at least 1000 L.

In a preferred embodiment of the invention, the process is carried out in a batch-wise fashion. In a batch process according to this invention, the lactate content of in the fermentation broth will gradually increase provided the pH drop is prevented by the addition of the one or more alkalization agents. Still, at some point the "limiting lactate concentration" may be reached, which is the lactate concentration (concentration of undissociated and dissociated lactic acid) at which, under a given set of incubation conditions (pH, nutrient medium, temperature, degree of aeration), further lactate production is inhibited. In other words, growth and/or lactate material production may stop due to the accumulation of one or more fermentation products as well as in response to the pH drop resulting from the production of fermentation products, i.e. the fermentation reaction has a self limiting point for the given set of incubation conditions. The present inventors established that the nisin content typically reaches its maximum before the fermentation reaction has reached the self-limiting point and may decrease if fermentation is continued beyond said point. In the present process, the incubation step is typically stopped before the point where the concentration of lactate equivalents reaches 25 g/L, preferably 24 g/L, more preferably 23 g/L, more preferably 22 g/L. Preferably, the incubation step is allowed to proceed to the point where the concentration of lactate equivalents exceeds 15 g/L, more preferably 17 g/l, more preferably 18 g/L, more preferably 19 g/L, most preferably 20 g/l. The present process typically results in the production of a broth containing a final concentration of nisin of at least 1000 IU/ml, preferably at least 2000 IU/ml, and more preferably at least 2500 IU/ml, e.g. about 3000 IU/ml.

In a preferred embodiment of this invention, the fermentation process is stopped by the addition to the fermentation broth of an amount of acid, in particular lactic acid, sufficient to stop lactate production. A process is accordingly provided as defined in the foregoing, wherein step c) is followed by a step d1) comprising adding an amount of acid to reduce the pH of the fermented broth to below 6, preferably to below 5.5, preferably to below 5, e.g. to 4.7. In a particularly preferred embodiment said acid is lactic acid. The lactic acid will typically be added in concentrated or dilute liquid form, such in the form of an aqueous solution having a lactic acid content of at least 100 g/l, although the invention is not particularly limited in this respect. This step of acidification of the fermentation broth by the addition of acid has been found to significantly improve the overall nisin yield and/or to improve the nisin stability during subsequent treatments involving heating of the composition.

After incubation of the inoculated nutrient medium for a period sufficient to reach the desired lactate and nisin levels and, optionally, after stopping the fermentation by the addition of an acid, the fermentation broth is typically subjected to a further treatment aimed at the inactivation of the lactic acid bacteria, by heat-treatment. A process is accordingly provided as defined herein before, comprising the additional step d2) of heating the fermentation broth obtained after step c) or d1) by subjecting it to a temperature of at least 40° C., at least 45° C., or at least 50° C., for a period of at least 10, at least 20, at least 30, at least 40 or at least 50 minutes, so as to inactivate the lactic acid bacteria.

The fermentation broth obtained using the present invention can be processed into a suitable product formulation simply by removing water, typically to obtain a paste. The lactate will be present mainly as mixture of sodium and calcium salts and the present inventors have established that these ferments can suitably be concentrated to dry solids contents of 30 wt % and more without the problem of salts crystallizing out of the product. The present inventors, furthermore, found that processing of the ferment into a concentrated form in accordance with this embodiment, gave particularly advantageous results in terms of the quality of the resulting product, especially in terms of (final) nisin activity and/or organoleptic properties. Hence, in an embodiment of the invention, a process is provided as described herein before, comprising the additional step e) of concentrating the ferment obtained in step c), d1) or d2) to a paste having a dry solids content of at least 30 wt. %, preferably within the range of 30-50 wt. %. Any conventional process can be used to perform step e). In a preferred embodiment step e) is performed by subjecting the ferment obtained in step c), d1) or d2) to an environment of above-ambient temperatures, typically to an environment of 55-70° C., and, preferably, reduced pressure, e.g. at a pressure of 190-250 mbar. For performing this step conventional equipment can be used that one of average skill is well-acquainted with.

In one embodiment, following step e), the concentrated liquid or paste is quickly cooled to a temperature of below 40° C., preferably below 30° C., more preferably below 20° C., more preferably to a temperature of below 10° C. The present inventors established that this step significantly aids to the quality of the resulting product, especially the (final) nisin activity and/or the organoleptic properties, e.g. compared to products that are not quickly cooled after step e). An embodiment of the invention is accordingly provided comprising a step f) wherein the concentrated liquid or paste obtained in step e) is cooled to a temperature of below 40° C., preferably below 30° C., more preferably below 20° C., more preferably to a temperature of below 10° C., typically by placing it in an environment of below ambient temperatures for a period sufficient to accomplish the above recited lowering of the temperature. In a particularly preferred embodiment this step comprises placing the composition in a cooling or refrigerating apparatus operated at a temperature of less than 15° C., less than 10° C. or less than 5° C. Preferably, during this step, the concentrated liquid or paste is agitated in order to avoid accumulation of material on parts of the equipment.

Alternatively, the fermentation broth obtained using the present invention can be processed into a free flowing powder product by evaporation of substantially all of the water. Such powders, containing anhydrous calcium lactate in combination with sodium lactate as the bulk of the powder, combine high stability with excellent rehydration/dissolution behavior. In particular, ferments obtained in accordance with the invention, in this regard, have superior properties compared to ferments containing only calcium lactate as the major lactate salt.

Hence, in an embodiment of the invention, a process is provided as described herein before, comprising the additional step e') of subjecting the ferment obtained in step c), d1) or d2) to a drying step to produce a dry powder composition having a water content of less than 10 wt. %, preferably less than 5 wt. %, more preferably less than 3.5 wt %. In one embodiment the step e') comprises spray-drying of the ferment, to produce a free-flowing powder product. Preferably drying of the aqueous liquid comprises spray drying of the aqueous liquid. In the present method, prior to the spray drying, aqueous liquid may be concentrated by evaporation. Preferably, the aqueous liquid has a dry matter content of 1-80 wt. %, most preferably of 10-60 wt. % when it is fed into a spray dryer.

Alternatively, a powder may be produced by first drying the aqueous liquid to produce a dry residue, e.g. by means of drum drying) and subsequently reducing the size of the dry residue by, for instance, grinding, milling or cutting. In an embodiment of the invention, a ferment may be concentrated and optionally cooled in accordance with steps e) and f) as described above, before being subjected to a further drying step e') to produce a dry powder composition.

Owing to the use of the one or more alkalizing agents comprising alkaline sodium and calcium salts in the above recited relative amounts, the present invention allows for the production of ferments, including dairy based ferments, that do not need any clarification processing or other type of processing aimed at the removal of certain (solid) components from the fermentation broth in order to obtain an acceptable food-grade preservative product. Hence, in a preferred embodiment of the present invention, a process as defined herein before is provided, wherein the fermentation broth is not subjected to a processing step wherein dissolved or non-dissolved solid matter is removed from the fermented broth following step c), i.e. regardless of the application of the optional steps d), e) and/or f).

Another aspect of the invention, concerns a lactate ferment product obtainable by the processes as defined herein above. The use of the one or more alkalization agents described herein results in a product containing lactate mainly in the form of sodium and calcium lactate, which confers certain advantageous properties to the fermentation products, especially with regard to the ability to process such fermentation products into various liquid, semi-liquid and solid formulations and/or with regard to the organoleptic properties of these fermentation products.

In a particularly preferred embodiment of the invention, the lactate ferment product contains at least 25 wt. % of lactate, on the basis of dry solids weight, more preferably at least 40 wt. %, most preferably at least 50 wt. %. As will be understood, this includes all forms of lactate, including free lactic acid as well as lactate containing salts.

Typically, in the lactate ferment product of the invention the major part of the lactate is in the form of sodium and calcium salts. Hence, in a preferred embodiment, a lactate ferment product as defined herein is provided comprising lactate anions and sodium and calcium cations, wherein the amount of sodium and calcium cations exceeds 0.5 of the stoichiometric equivalent, preferably it exceeds 0.75 of the stoichiometric equivalent, more preferably it exceeds 0.9 of the stoichiometric equivalent. Furthermore, in a preferred embodiment, a lactate ferment product as defined herein is provided comprising lactate anions and sodium and calcium cations, wherein the amount of sodium and calcium cations is equal to or less than 1.0 of the stoichiometric equivalent. As will be understood by those skilled in the art, the stoichiometric equivalent refers to the combined amount of sodium and calcium cations that would theoretically be necessary to provide counterions for all lactate anions.

As indicated herein before, in an embodiment, the product will typically contain sodium and calcium ions in a Na:Ca ratio (w/w) within the range of ⅙-½. In a more preferred embodiment of the invention, the Na:Ca (w/w) ratio is within the range of 1/5.5-1/2.5, most preferably, the Na:Ca (w/w) ratio is within the range of ⅕-⅓, e.g. ¼.

In a particularly preferred embodiment, as will be understood from the foregoing, the lactate ferment product contains appreciable levels of nisin. Hence, in a preferred embodiment of the invention, a lactate ferment product as defined herein before is provided containing at least 0.10 mg nisin per g of dry matter, more preferably at least 0.20 mg nisin per g of dry matter, most preferably at least 0.25 mg nisin per g of dry matter. It is to be understood that nisin actually denotes several nisin variants, such as nisin A and nisin Z, which differ in their amino acid sequence, typically only by a single amino acid. The most common variant being nisin A. The type of nisin produced will depend solely on the choice of the bacterial strain used for fermentation. The strains preferred in the context of the present invention will typically produce nisin A. Hence, the nisin is preferably nisin A. The recited amounts of nisin, as will be understood by those of average skill, applies equally to all nisin variants.

Furthermore, it is to be noted that herein it is assumed that 1 microgram of nisin equals 40 Hence the preferred levels of nisin correspond to activities of at least 400 IU, at least 800 IU and at least 1000 IU, all per g of dry matter, respectively.

Further aspects of the present invention concerns the use of a lactate ferment product as defined in any of the foregoing for the preservation of an alimentary product, especially a food product or a beverage, more in particular a product selected from the group consisting of processed and natural cheeses, cooked meats, canned foods, seafoods, alcoholic beverages, dairy deserts, dairy drinks/liquids, prepared meals, dressings, sauces, flour based products, liquid egg products, etc.; and to methods of preserving such alimentary products comprising the step of incorporating therein or applying thereon a lactate ferment product as defined in any of the foregoing. The lactate ferments of the invention are particularly useful in the preservation against spoilage by a microorganism, especially a microorganism selected from the group consisting of Listeria spp, clostridium spp, lactic acid bacteria and bacillus spp. It is within the purview of those of ordinary skill in the art to determine the most appropriate dosages for optimal protection against spoilage while avoiding negative impact on other quality aspects of the alimentary product, especially organoleptic properties. As explained before, the present lactate ferment products can be applied in relatively high dosages without negative impact on organoleptic properties and salt content.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way

EXAMPLES

Example 1

Batch flasks (2 L) are used as reactors for fermentation. This reactor is sterilized empty for 20 min at 121° C. All cultivations are performed aseptically. Whey powder 5% w/w and Yeast extract 0.2% w/w (based on dry weight) is used as the nutrient medium (pasteurized for 30 min at 80° C. inside the reactor) for all fermentations. A mixture of $Ca(OH)_2$/NaOH (composition in table below) is used to control the pH, which is kept at approximately pH, 5.5.

A first batch flask containing the nutrient medium is inoculated from a glycerol stock of Lactococcus lactis ATCC 11454 and incubated overnight at 30° C. The inoculum is 2.5% w/w. During exponential growth phase ferment from the first batch flask is transferred as inoculum for the next 2 L reactor containing nutrient medium, which is ran under the same conditions. The fermentation in the second reactor is stopped after the lactate concentration had reached more than 25 g/l. Around 10 ml of lactic acid (80% dry solids) is sufficient to lower the pH to 4.7. The reactor is kept at 50° C. for 1 hour for inactivation. After that, the ferment is cooled. Final Nisin amount is around 3000 IU/ml.

| Alkalization agent | NaOH | $Ca(OH)_2$ |
|---|---|---|
| Concentration in pure stock (%) | 50.0 | 25.0 |
| Proportion in base (%) | 10.5 | 89.5 |
| Final concentration in base (%) | 5.3 | 22.4 |
| $Ca^{2+}/Na^+$ ratio (—) | | 4.0 |

The ferment can be further purified and/or concentrated according to methods known to a person skilled in the art. By means of evaporation e.g. a paste or concentrate can be prepared. By means of spray drying e.g. a powder can be prepared.

A paste produced by evaporation of a ferment as prepared above, with a dry matter content of 35.2%, comprised nisin with an activity of 67064 IU/g (based on 100% DM).

The ferment is examined for various properties, such as the stability of the nisin activity in the ferment as well as in concentrates thereof and the organoleptic properties of the ferment. The ferments and concentrates have sufficient stability of nisin activity to allow for transportation and storage of the product in accordance with usual industry practice. The incorporation of the ferment and/or concentrates thereof in various alimentary products at effective dosages results in organoleptic properties that are generally favoured over those obtained with prior art nisin ferments.

Example 2

Lactic acid ferment is produced according to the procedure of example 1. The raw ferment is not purified and processed into a powder by spray-drying.

Products with anhydrous calcium lactate were obtained by drying at a product temperature during the spray-drying process of 90° C., whereas the air temperature varies between 165 and 180° C.

Products with calcium lactate pentahydrate were obtained using the spray granulation technique using a continuously operating fluidized bed. The product temperature was 60° C., the temperature of the fluidization air was 110° C.

For dissolution tests 2 g of a powder was accurately weighed in a plastic cup and two glass beads with a diameter of 6 mm were added. The blend was manually mixed for 1 min. To prevent water uptake, the air was purged with dry nitrogen. Dissolution tests were performed by adding the powder sample to 198 g demineralized water which was stirred with a stirring flea. The test conditions are such that sink conditions are always fulfilled (i.e. after complete dissolution of the material the concentration in the liquid is less than around 30% of the saturation solubility) Times to reach 10%, 50%, 90% and 95% of complete dissolution were calculated.

For stability tests samples are stored in hermetically sealed glass jars to prevent any moisture exchange. The samples have been stored at temperatures of 4° C., room temperature (around 18-22° C.) and 40° C. The properties of the powders are visually assessed at different time-points. The ferment powder is stable when it remains a free-flowing powder.

It is possible to neutralize the fermentation broth using calcium hydroxide (Ca(OH)$_2$), sodium hydroxide (NaOH) or a combination thereof. This leads to a certain calcium to sodium (Ca/Na) ratio in the final product. A solid product containing only Na is not suitable because of high Na content and unacceptable hygroscopicity of the dry product. A solid product with anhydrous calcium lactate and with a high Ca/Na ratio of 20 has been produced. This product suffered from the disadvantage of unacceptable taste and long dissolution time (95%) of 88 s.

A product with calcium lactate pentahydrate and a Ca/Na ratio of 3-4 was acceptable from a taste and Na content perspective. Dissolution time (95%) of this product is around 30 s, which is acceptable. However, the product lacked sufficient stability. This is because the calcium lactate is present in the form of calcium lactate pentahydrate. Sodium lactate, which is also present, presumably, was able to extract the crystal water from calcium lactate pentahydrate crystals. This leads to dissolution of sodium lactate in the water extracted from calcium lactate and, as a result of that, paste formation, even when packed in aluminum sachets.

It has been found that a product with calcium lactate anhydrate and sodium lactate (in a Ca/Na ratio of 3) still has an acceptable dissolution time (95%) of 31 s. Stability proved acceptable as well, as paste formation did not occur. The composition of this product was as follows:

| | |
|---|---|
| Total Nisin Activity (based on 100% DM, IU/g) | 59082 |
| Lactic Acid (% w/w) | 51 |
| Succinic Acid (% w/w) | 1.12 |
| Total Nitrogen (% w/w) | 1.6 |
| Na (% w/w) | 2.9 |
| Ca (% w/w) | 8.1 |
| Lactose (% w/w) | 11 |
| pH (10%) | 4.7 |

Example 3

In order to test for the taste impact of calcium and sodium in the neutralization agents, model products have been prepared. Milk was used as the reference product. Different samples have been prepared, consisting of milk to which nisin and/or lactate ferments have been added with different concentrations of calcium and sodium, as presented in the table below.

| Code | Blanc | Na-based | Ca-based | Model A | Model B | Model C |
|---|---|---|---|---|---|---|
| pH | 6.73 | 6.77 | 6.7 | 6.71 | 6.69 | 6.7 |
| Na added | 0 | 0.97 | 0.06 | 0.16 | 0.32 | 0.24 |
| Ca added | 0 | 0.08 | 1.25 | 0.89 | 0.39 | 0.65 |
| RATIO Ca:Na added | | 0.08:1 | 20:1 | 5.4:1 | 1.2:1 | 2.7:1 |

These samples were tested by a panel. The results are analyzed by means of Principal Component analysis and summarized in a Bi-Plot (cf. B. S. Everitt, An R and S-Plus Companion to Multivariate Analysis). The Bi-Plot is depicted in FIG. 1.

From the results, it is clear that the use of sodium as the sole counterion in the neutralization agent (Na-based) leads to a salty taste, whereas the use of calcium as the sole counterion (Ca-based) lead to an astringent and bitter taste. By using both calcium and sodium in a ratio of between approximately 1:1 and 6:1 w/w a much more neutral taste can be achieved.

The invention claimed is:

1. A process of producing a nisin-containing lactate ferment in dry powder form, comprising the consecutive steps of:
    (a) inoculating a nutrient medium comprising a solution of a fermentable substrate and a nitrogen source in an aqueous medium with nisin producing lactic acid bacteria; and
    (b) incubating the inoculated nutrient medium under conditions favorable to the growth and/or metabolic activity of said lactic acid bacteria for a period sufficient to produce a fermentation broth containing at least 20 g/l of lactate equivalents and/or at least 1000 IU/ml of nisin equivalent activity, during which period the pH of the fermentation broth is controlled by addition of one or more alkalization agents comprising sodium hydroxide and calcium hydroxide, wherein the Na:Ca (w/w) ratio of the added hydroxides is between ⅙ 1/1; and
    (c) spray drying the ferment obtained in step (b) to obtain a free flowing powder containing anhydrous calcium lactate in combination with sodium lactate as the bulk of the powder, by evaporating substantially all water.

2. The process according to claim 1, wherein the Na:Ca (w/w) ratio of the added salts is between ⅙ ½.

3. The process according to claim 1, the pH of the fermentation broth is maintained between 4.8 to 6.0.

4. The process according to claim 1, wherein the nutrient medium comprises a dairy product.

5. The process according to claim 1, wherein the inoculation medium comprises activated lactic acid bacteria.

6. The process according to claim 1, further comprising (b') acidifying the fermentation broth by adding an acid in an amount sufficient to reduce the pH of the fermentation broth to below 4.8 before step (c).

7. The process according to claim 6, wherein the acid is lactic acid.

8. The process according to claim 1, further comprising inactivating the lactic acid bacteria by subjecting the fermentation broth to a temperature of at least 40° C. for a period of at least 10 minutes before step (c).

9. The process according to claim 1, wherein step (c) comprises concentrating the ferment to a concentrate having a dry solids content of at least 30 wt. %.

10. The process according to claim 9, further comprising (d) cooling the concentrate to a temperature of below 40° C.

11. The process according to claim 1, wherein the powder has a water content of less than 5 wt %.

12. The process according to claim 1, wherein the nutrient medium comprises whey.

13. The process according to claim 1, which does not comprise a step of removing non-dissolved matter from the fermented broth.

14. A ferment produced by the process according to claim 1.

15. The ferment according to claim 14, containing at least 0.25 mg nisin per gram of dry matter.

16. A method of preserving an alimentary product, comprising adding the ferment of claim 14 to the product.

17. The process according to claim 1, wherein the spray drying is after acidification of the fermentation broth and/or subjecting the fermentation broth to a temperature of at least 40° C. for a period of at least 10 minutes, to obtain a free flowing powder.

18. A process of producing a nisin-containing lactate ferment, comprising the consecutive steps of:
   (a) inoculating a nutrient medium comprising a solution of a fermentable substrate and a nitrogen source in an aqueous medium with nisin producing lactic acid bacteria; and
   (b) incubating the inoculated nutrient medium under conditions favorable to the growth and/or metabolic activity of said lactic acid bacteria for a period sufficient to produce a fermentation broth containing at least 20 g/l of lactate equivalents and/or at least 1000 TU/ml of nisin equivalent activity, during which period the pH of the fermentation broth is controlled by addition of one or more alkalization agents comprising sodium hydroxide and calcium hydroxide, wherein the Na:Ca (w/w) ratio of the added hydroxides is between $1/6$ $1/1$, wherein the pH of the fermentation broth is maintained between 5.0 to 6.0 in step (b); and
   (c) evaporating substantially all water from the ferment to obtain a free flowing powder containing anhydrous calcium lactate in combination with sodium lactate as the bulk of the powder.

\* \* \* \* \*